United States Patent [19]
Ulrich

[11] Patent Number: 5,409,488
[45] Date of Patent: Apr. 25, 1995

[54] SPONDYLODESIS IMPLANT

[76] Inventor: Heinrich Ulrich, Galgenbergweg 28, Ulm/Donau, Germany

[21] Appl. No.: 107,808
[22] PCT Filed: Apr. 2, 1991
[86] PCT No.: PCT/AU91/00122
§ 371 Date: Aug. 20, 1993
§ 102(e) Date: Aug. 20, 1993
[87] PCT Pub. No.: WO93/13722
PCT Pub. Date: Jul. 22, 1993

[30] Foreign Application Priority Data
Jan. 16, 1992 [DE] Germany ............. 42 00 904.9

[51] Int. Cl.⁶ .............................................. A61B 17/56
[52] U.S. Cl. ....................................................... 606/61
[58] Field of Search .................. 606/61, 60, 53, 73

[56] References Cited
U.S. PATENT DOCUMENTS
5,176,679 1/1993 Lin ........................... 606/61

FOREIGN PATENT DOCUMENTS
0443894 8/1991 European Pat. Off. ........ 606/61
3132520 6/1982 Germany ...................... 606/61
3841008 6/1990 Germany ...................... 606/61

Primary Examiner—Tamara L. Graysay
Attorney, Agent, or Firm—Herbert Dubno; Yuri Kateshov

[57] ABSTRACT

The spondylodesis implant has two connection pieces guided on respective threaded spindles and adjustable as to their mutual distance and resetting screws for which for the fastening of the connection pieces to the vertebrae receiving elements are provided in the connection pieces, a further connection piece between the other pieces and provided with a respective receiving element, the threaded spindles being supported on the further connection piece so that they are independently rotatable and axially nondisplaceable and being inclined with respect to each other in the common plane of their axes.

6 Claims, 4 Drawing Sheets

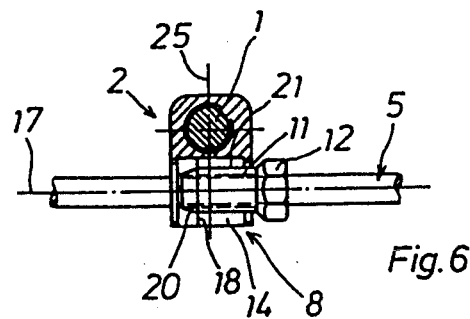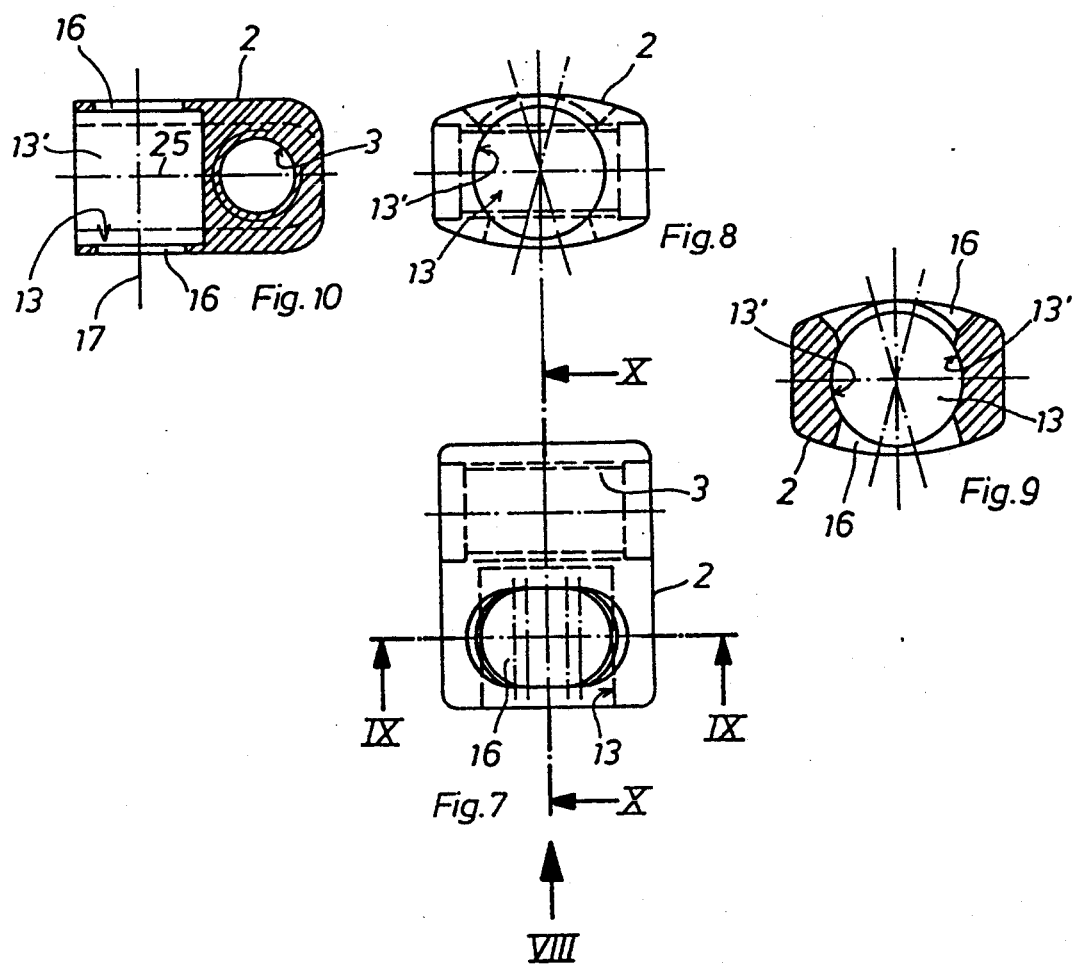

SPONDYLODESIS IMPLANT

CROSS REFERENCE TO RELATED APPLICATIONS

This is national phase application PCT/DE93/00031 filed 13 Jan. 1993 and based in turn, upon German national application P 42 00 904.9 filed 16 Jan. 1992 under the International Convention.

FIELD OF THE INVENTION

The invention relates to a spondylodesis implant for the correction and fixation of the relative position of vertebrae, with two connection pieces guided in threaded spindles in the longitudinal direction of the spinal column and adjustable as to their distance from each other, and with resetting screws which can be screwed into the vertebrae, for which receiving elements are provided in the connection pieces for the purpose of fastening the connection pieces to the vertebrae.

BACKGROUND OF THE INVENTION

The spondylodesis implant of this kind known from DE 31 32 520 A1 serves for the adjustable fixation of two immediately adjacent vertebrae. The threaded spindles assigned to the two connection pieces are made in one piece in a coaxial arrangement, whereby between the two threaded spindles a connecting outer hexagonal piece is provided, which serves for the application of a turning tool for the common rotation of the threaded spindles. The threaded spindles as well as the corresponding threaded nuts by means of which the connection pieces are guided on their respective threaded spindles rotate in opposite senses, so that during the concurrent rotation of the threaded spindles the two connection pieces are either moved towards each other or away from each other according to the direction of rotation.

OBJECTS OF THE INVENTION

It is the object of the present invention to provide a spondylodesis implant so that three successive vertebrae can be corrected and fixated still another object is to provide a spondylodesis implant for the mutual displacement of the vertebrae.

SUMMARY OF THE INVENTION

According to the invention an implant provides between the two connection pieces a further connection also equipped with a receiving element for a resetting screw, whereby on this median connection piece the threaded spindles for the two outer connection pieces are supported so that they are independently rotatable and axially nondisplaceable. The two threaded spindles are inclined with respect to each other in the common plane of their axes thereby adjusting the implant to the sagittal curvature of the spinal column. Preferably the mutual inclination of the threaded spindles is of approximately 15°.

When such implant is affixed with each of its connection pieces to one of three successive vertebrae, by rotating the threaded spindles, the two outer vertebrae can be independently set and fixated with respect to the middle vertebra mutual inclination of the two threaded spindles takes into account to follow the natural curvature of the spinal column in the area of the three vertebrae interconnected by the implant.

The preferred embodiment is characterized in that the threaded spindles are guided each by a pivot pin in a pivot opening of the median connection piece and have on the pivot pin an annular groove coaxial with the spindle axis. A projection on the side of the connection piece engages in the groove to secure the threaded spindle against axial displacements. This projection consists suitably of a cross pin stuck into the connection piece and tangentially reaching into the annular groove. It is therefore advisable that each threaded spindle be equipped with key faces for the application of turning tools between its threaded shaft and the connection piece supporting it. Suitably the key faces on each threaded spindle form an outer hexagon in one piece with the threaded spindle.

The resetting screws can be the usual bone screws provided with a screw head, whereby the screw head comes to lie on the connection piece when the screw is tightened. However, more frequently the headless resetting screw with a smooth shaft segment succeeding the threaded shaft portion will be used within the framework of the invention, since, after being screwed into the respective vertebra, it can still be shortened to the length desired for the fastening of the connection pieces. It is advantageous to select an arrangement within the framework of the invention wherein the resetting screws in their receiving spaces run basically parallel to the axes of the two threaded spindles, whereby the resetting screws are guided in their respective receiving spaces so that they are displaceable in the longitudinal screw direction and pivotable transversely thereto, and that the receiving elements are equipped with a clamping device actuatable by a clamping member, which in the clamped position secures the resetting screw against displacement or pivoting in the receiving element.

BRIEF DESCRIPTION OF THE DRAWING

The above and other objects, features, and advantages will become more readily apparent from the following description, reference being made to the accompanying drawing in which:

FIG. 6 is a section in the direction IV—IV through the implant according to FIGS. 1 and 2, FIG. 7 is a top view only of the connection piece of the object in FIG. 6, FIG. 8 is a frontal view of the connection piece of FIG. 7 in the direction of the therein indicated arrow VIII, FIG. 9 is a sectional view of the piece along the section IX—IX in FIG. 7.

FIG. 10 is a sectional view of connection view along the section X—X in FIG. 7;

FIGS. 1 and 2 show the spondylodesis implant wherein on threaded spindles 1 connection pieces 2 are guided, which are adjustable as to their distance from each other by rotating the threaded spindles 1. Altogether three connection pieces 2, 2' are provided, whereby the middle connection piece serves for the support of the two lateral connection pieces so that they are independently rotatable and axially nondisplaceable Thereby the two threaded spindles 1 are inclined with respect to each other at an angle 30 of approximately 15° in the common plane of their axes, which corresponds with the plane of the drawing, in order to make possible the adjustment of the implant to the sagittal curvature of the spinal column. The threaded spindles 1 are each guided by means of a pivot pin 31 in a pivot opening 32 of the median connection piece 2' and are provided on the pivot pin 31 with an annular groove 33 coaxial with the spindle axis, wherein a cross pin 34 stuck into a bore in the connection piece 2' engages tangentially and secures the threaded spindle 1 against axial displacement. Between its threaded shaft and the median connection piece 2' supporting it, each threaded spindle 1 is equipped with key faces for the application of a turning tool, whereby these key faces on each threaded spindle 1 form together with the threaded spindle a solid outer hexagon 4. For connecting the connection pieces 2, 2' each with one vertebra not shown in the drawing serve the bone screws 5, which are screwed into the vertebra with the threaded segment 6 and are held with the smooth, threadless shaft segment 7 in a receiving space generally marked 8 on each connection piece. These receiving spaces 8 for the resetting screws 5 have the same design in all three connection pieces 2, 2'. Thereby the resetting screws 5 are slidably guided in the respective receiving element 8 with the threadless smooth shaft segment 7 in the longitudinal screw direction and also pivotably in a transverse direction thereto indicated by arrow 10. Besides the receiving elements 8 are equipped with a clamping mechanism actuated by a clamping member which in the clamped position locks the resetting screws 5 against displacement as well as pivoting in the receiving element 8. The clamping member is a threaded sleeve 11, which is again equipped with a hexagon 12 for actuation by means of a key. In the following only the receiving element 8 for one of the lateral connection pieces 2 is described.

Figure 1:
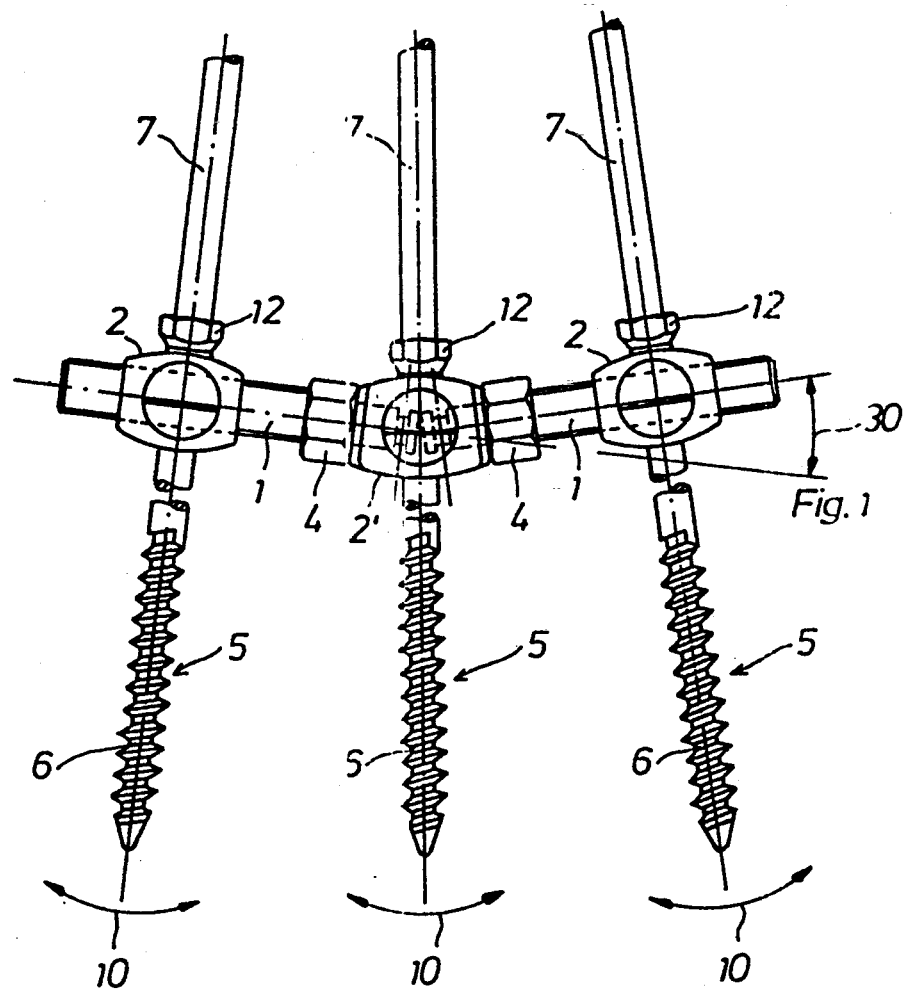
FIG. 1 is a lateral view of a spondylodesis implant according to the invention.
Figure 2:
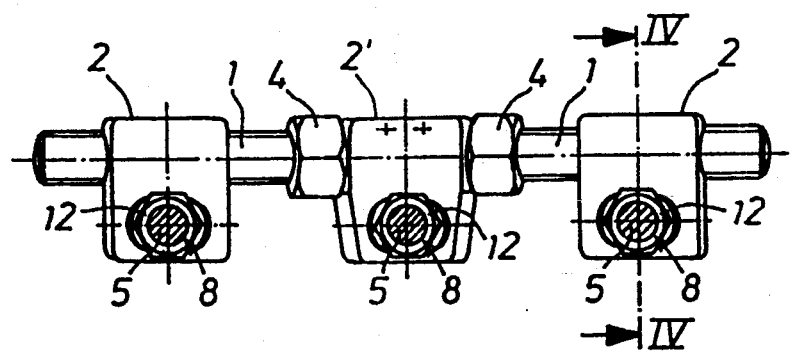
FIG. 2 is a top view of the implant according to FIG. 1.
Figure 5:
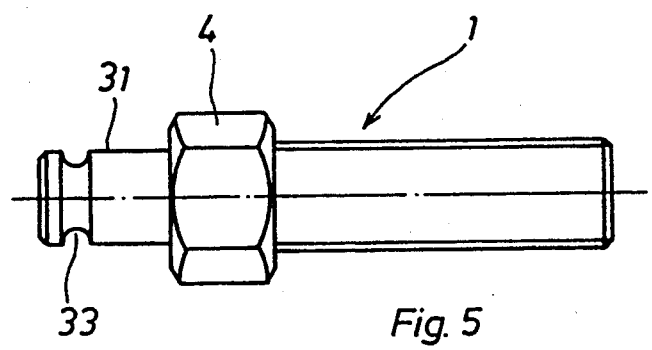
FIG. 5 is one of the threaded spindles of the implant according to FIGS. 1 and 2 in a lateral view.
Figure 4:
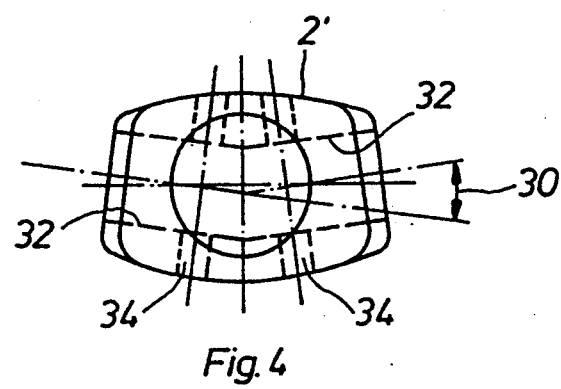
FIG. 4 is the lateral view of the connection piece according to FIG. 3.
Figure 3:
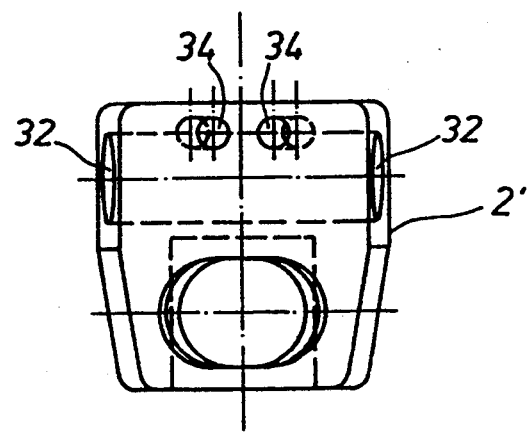
FIG. 3 is a top view only of the median connection piece of the implant according to FIG. 1 and FIG. 2 in an enlarged representation.
Figures 11, 13:
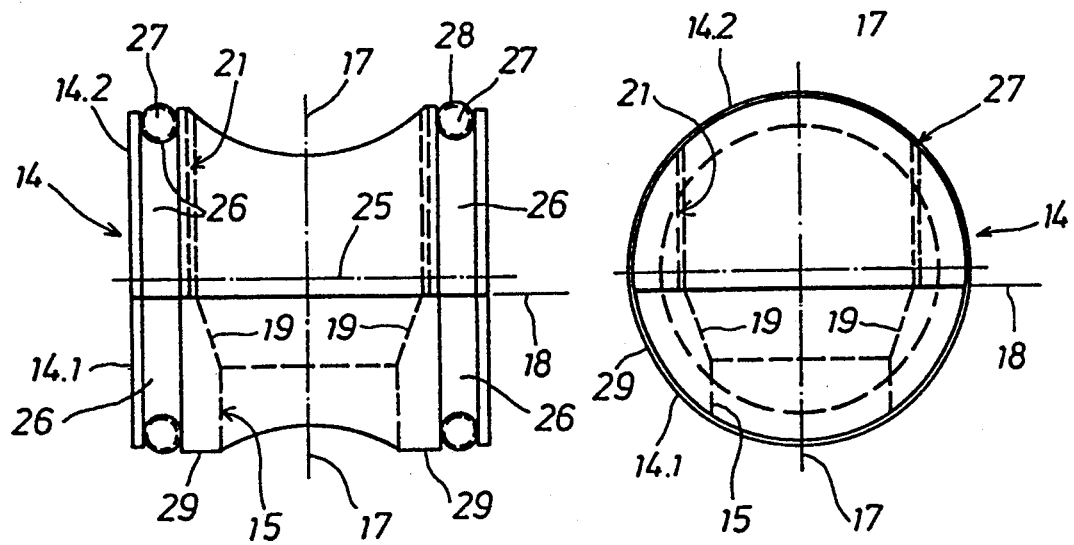
FIG. 11 is the link body of the object in FIG. 6 together with the spring rings in a lateral view.
FIG. 13 is the spring rings in FIG. 11 in an axial view.
Figure 12:
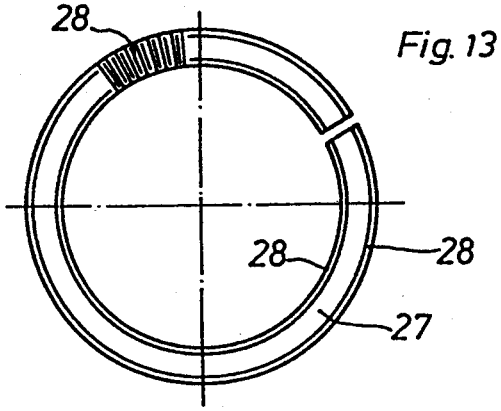
FIG. 12 is an axial view of the spring shown in FIG. 11.
Figure 14:
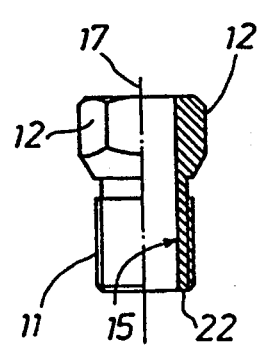
FIG. 14 is the threaded sleeve.
Figure 15:
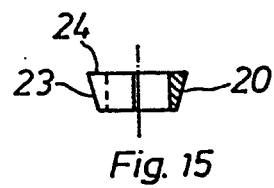
FIG. 15 is the clamping ring of the object in FIG. 6, partially in a lateral view and partially in section.
Figure 16:
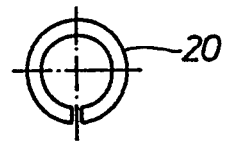
FIG. 16 is an axial view of the clamping ring according to FIG. 15.

In the connection piece 2 a pivot opening 13 for a link body 14 is formed, and in the link body 14 a guide channel 15 is shaped for the resetting screw 5. On both sides of the link body 14 the resetting screw 5 projects from the connection piece 2 through the openings 16 provided in the walling of the connection piece 2. The link body 14 is divided in two across the axis 17 of the guide channel 15 in the plane 18. In one part 14.1 of the two parts 14.1 and 14.2 a conical seat 19 coaxial with the guide channel 15 is formed and in this seat a peripherally slotted clamping ring 20 is located. In the braced state the clamping member, namely the threaded sleeve 11 forces the two link body parts 14.1, 14.2 in the pivot opening 13 against the opening surface 13' on the one hand and on the other hand it forces the clamping ring 20 in the conical seat 19 against the resetting screw 5. This is achieved in a simple manner due to the fact that the conical seat 19 abuts with its enlarged end in the gap 18 between the two link body parts 14.1, 14.2 and that the link body part 14.2 which is opposite to this abutment is provided with a threaded bore 21 coaxial with the guide channel 15, wherein the threaded sleeve 11 which forms a segment of the guide channel 15 is guided. The threaded sleeve 11 pushes with the sleeve end 22 lying within the link body 14 against the clamping ring 20 in the conical seat 19 and with the other sleeve end projects outwardly with the hexagon collar 12 positioned there through the opening 16, so that the hexagon collar 12 is accessible for the actuation of the threaded sleeve 11. The clamping ring 20 has an outer conical surface 23 suited to fit the conical seat 19. The rim 24 of the clamping ring 20 has an outer diameter at least as large as the one of the ends 22 of the threaded sleeve 11. As a result the threaded sleeve always rests against the facing rim 24 of the clamping ring 20. When the threaded sleeve 11 is tightened, the clamping ring 20 in the conical seat 19 is braced against the threadless shaft portion 7 of the resetting screw 5; at the same time, due to the threaded sleeve 11 resting against the clamping ring 20, the two link body parts 14.1, 14.2 are pushed apart and are thereby locked in pivot opening 13.

In the embodiment examples the link body 14 and the pivot opening 13 are cylindrically shaped with a cylinder axis 25 being perpendicular to the axis 17 of the guide channel 15. The pivotability of the link body only about this sole axis 25 is sufficient in the case of the embodiment examples, since the connection pieces 2 themselves are rotatable about the axis of the spindles guiding them, and for this reason are capable to adjust to the inclination of the resetting screws 5 in the direction of this rotation on the guide spindle 1. But in principle, in the case of implants with a differently designed guidance system of the connection pieces 2, it is of course possible to provide pivot openings and corresponding link bodies, for instance ball joint bodies, which can perform also a rotation about two axis perpendicular with respect to each other. However, in this case the construction of such a receiving element 8 is more expensive. In the present case of only cylindrical link bodies there is a particularly simple way to insure that a very efficient locking of the link body 14 in the pivot opening 13 and thereby a fixation of the resetting screws 5 secured against pivoting is achieved. For this purpose on both sides of guide channel 15, at the outer peripheral surfaces of the link body 14, annular grooves 26 are formed coaxially with the cylinder axis 25 with peripherally slotted spring rings 27 being embedded therein, provided on the outside with crossribbing 28 and projecting radially with the ribs slightly over the peripheral cylinder surface 29 of the link body 14. This crossribbing 28 is achieved in a simple manner by providing the spring ring 27 with a threading. If during the actuation of the threaded sleeve 11 the two link body parts 14.1, 14.2 are pushed apart, they are braced against the pivot opening surface 13' of the pivot opening 13 via spring rings 27, whereby their ribs embed themselves in the pivot opening surface 13' on the one hand and in the walling of the annular grooves 26 on the other hand.

I claim:

1. An implant for fixation and correction of the relative position of vertebrae, the implant comprising:

a plurality of connection pieces spaced apart in a longitudinal direction of a spinal column, at least one of said plurality of the connection pieces being spacedly flanked by a respective pair of adjacent outer connection pieces, each of said plurality of connection pieces being formed with:

a respective receiving element, and a respective resetting screw received in the respective receiving element and extending therethrough transversely to the longitudinal direction to engage in the column;

means for adjusting a distance between the outer connection pieces and including:

a pair of threaded spindles each mounted on the respective outer piece and extending longitudinally along a respective spindle axis toward the one connection piece, a pair of pins each formed on the respective spindle and provided with a respective annular groove coaxial with the respective spindle;

said one connection piece being formed with a pivot opening receiving the pins of the spindles which are mounted rotatably independently and inclined toward one another in a plane common to the axes to adjust the implant to the sagittal curvature of the spinal column; and a pair of stops on the one connection piece engaging the respective grooves to arrest axial displacement of the spindles upon adjusting the distance between the outer pieces.

2. The implant defined in claim 1 wherein said spindles form an angle of approximately 15°.

3. The implant defined in claim 1 wherein each stop includes a respective cross pin mounted slidably on the one connection piece to engage tangentially in the respective groove.

4. An implant for fixation of bones, in particular for vertebrae, the implant comprising:

a plurality of connection pieces spaced apart in a longitudinal direction of a spinal column, at least one of said plurality of the connection pieces being spacedly flanked by a respective pair of outer connection pieces, each of said plurality of connection pieces being formed with:

a respective receiving element, and a respective elongated resetting screw mounted on the respective receiving element and extending transversely to the longitudinal direction to engage in the column, means for adjusting a distance between the outer connection pieces and including a pair of threaded spindles, each spindle being mounted on the respective outer piece and extending longitudinally along a respective spindle axis toward the one connection piece to be mounted thereon, said spindles being inclined toward one another in a plane common to the spindle axes upon mounting the spindles on the one connection piece, key face means operatively connected with each of the spindles for applying a turning tool between each of the outer and one connection pieces to rotate a respective one of the spindles independently from the other spindle, and stop means for axially arresting each of the spindles upon adjusting the distance between the outer connection pieces.

5. The implant defined in claim 4 wherein said key face means includes an outer hexagon formed unitarily with a respective one of the threaded spindles.

6. The implant defined in claim 4 wherein each of the resetting screw is longitudinally slidably guidable in the respective receiving element and is pivotal transversely to the screw's longitudinal dimension, each of the receiving elements being provided with:

respective locking means for securing the respective resetting screw against sliding and pivoting in a clamping position of the screw upon engaging the column, and a respective clamping member actuating the respective locking means.

* * * * *

UNITED STATES PATENT AND TRADEMARK OFFICE
CERTIFICATE OF CORRECTION

PATENT NO. : 5,409,488
DATED : 25 April 1995
INVENTOR(S) : Heinrich ULRICH

It is certified that error appears in the above-identified patent and that said Letters Patent is hereby corrected as shown below:

ON THE TITLE PAGE:
In the heading, line 22, change "Apr. 2, 1991" to read -- Jan. 13, 1993 ---;

Line 86, change "PCT/AU91/00122" to read -- PCT/DE93/00031 --.

Signed and Sealed this

Twelfth Day of September, 1995

Attest:

BRUCE LEHMAN

Attesting Officer    Commissioner of Patents and Trademarks